US011574707B2

United States Patent
Wickson et al.

(10) Patent No.: US 11,574,707 B2
(45) Date of Patent: Feb. 7, 2023

(54) SYSTEM AND METHOD FOR PHENOTYPE VECTOR MANIPULATION OF MEDICAL DATA

(71) Applicant: QuintilesIMS Incorporated, Danbury, CT (US)

(72) Inventors: Jonathan Wickson, West Sussex (GB); Robin Murray, High Peak (GB)

(73) Assignee: IQVIA Inc., Durham, NC (US)

( * ) Notice: Subject to any disclaimer, the term of this patent is extended or adjusted under 35 U.S.C. 154(b) by 673 days.

(21) Appl. No.: 15/478,282

(22) Filed: Apr. 4, 2017

(65) Prior Publication Data

US 2018/0285526 A1    Oct. 4, 2018

(51) Int. Cl.
*G16H 10/20* (2018.01)
*G16H 10/60* (2018.01)

(52) U.S. Cl.
CPC ............. *G16H 10/20* (2018.01); *G16H 10/60* (2018.01)

(58) Field of Classification Search
CPC .. G06Q 50/22–24; G16H 50/30; G16H 50/50; G16H 50/70; G16H 10/20; G16H 20/00; G16H 50/00
See application file for complete search history.

(56) References Cited

U.S. PATENT DOCUMENTS

| | | | | |
|---|---|---|---|---|
| 6,216,249 B1* | 4/2001 | Bliss | ................ | G11B 20/10009 714/792 |
| 6,417,802 B1* | 7/2002 | Diesel | .................... | G01S 19/26 342/357.31 |
| 2002/0065805 A1* | 5/2002 | Beals | .................... | G06F 16/288 |
| 2002/0119451 A1* | 8/2002 | Usuka | .................... | G16B 20/00 435/6.11 |
| 2004/0172267 A1* | 9/2004 | Patel | .................. | G06Q 10/0635 705/7.29 |

(Continued)

FOREIGN PATENT DOCUMENTS

CA        2732171 A1 *  3/2010  ............. G16H 50/30

OTHER PUBLICATIONS

Roque, Francisco S., et al. "Using electronic patient records to discover disease correlations and stratify patient cohorts." PLoS Comput Biol 7.8 (2011): e1002141. (Year: 2011).*

*Primary Examiner* — Linh Giang Le
*Assistant Examiner* — Constantine Siozopoulos
(74) *Attorney, Agent, or Firm* — John Maldjian; Stevens & Lee PC

(57) ABSTRACT

Cohort definition and selection system for a computer having a memory, a central processing unit and a display, the system including: a cohort definition module to configure the memory according to a phenotype vector. The phenotype vector includes a patient ID to uniquely associate the phenotype vector to a patient, a plurality of demographic dimension fields, each demographic dimension field to describe a respective demographic aspect of the patient, a calculated dimension field to describe a calculated information related to the patient, a plurality of phenotype-based dimension fields, each phenotype-based dimension field to indicate relevance of the respective phenotype-based dimension field to the patient, and a child phenotype vector to recursively define a phenotype-based dimension field, and a cohort selection module to select a set of phenotype vectors that are within a predetermined error from a cohort selection criteria.

21 Claims, 7 Drawing Sheets

(56) References Cited

U.S. PATENT DOCUMENTS

| | | | |
|---|---|---|---|
| 2006/0052945 A1* | 3/2006 | Rabinowitz | G16B 40/00 |
| | | | 702/20 |
| 2007/0192139 A1* | 8/2007 | Cookson | G06Q 10/10 |
| | | | 705/3 |
| 2007/0239551 A1* | 10/2007 | Zeller | G06Q 30/06 |
| | | | 705/26.63 |
| 2007/0260492 A1* | 11/2007 | Feied | G16H 10/60 |
| | | | 705/3 |
| 2011/0206246 A1* | 8/2011 | Wolf | G06K 9/00228 |
| | | | 382/118 |
| 2014/0257847 A1* | 9/2014 | Hu | A61B 5/742 |
| | | | 705/3 |
| 2015/0142331 A1* | 5/2015 | Beim | C12Q 1/6883 |
| | | | 702/19 |
| 2016/0275259 A1* | 9/2016 | Nolan | G06F 19/3418 |
| 2016/0283686 A1* | 9/2016 | Hu | G16H 50/20 |
| 2017/0199965 A1* | 7/2017 | Dekel | G16H 50/70 |
| 2018/0004803 A1* | 1/2018 | Hao | G06Q 10/04 |
| 2019/0057182 A1* | 2/2019 | Klement | C12Q 1/6886 |

\* cited by examiner

Simplified EMR Records

Person Structure

| PK | Gender | Age | Geography | BMI |
|---|---|---|---|---|
| 1 | M | 30 | BN43 | 22 |
| 2 | M | 45 | SE12 | 23 |
| 3 | M | 34 | BN12 | 26 |
| 4 | F | 37 | SO18 | 20 |

Event Structures

| FK | Event Type | Value1 | Value2 |
|---|---|---|---|
| 1 | Diabetes | Pos | - |
| 1 | Metformin | 6 | Pkts |
| 1 | Blood Test | 7 | % |
| 2 | Diabetes | Pos | - |
| 3 | Diabetes | Neg | - |
| 3 | Metformin | 10 | Pkts |
| 3 | COPD | Neg | - |
| 4 | COPD | Pos | - |
| 4 | Blood Test | 10 | MML |

FIG. 8B  Prior art

Standard Population Output

| PK | Gender | Age | Geography | BMI | Event Type | Value1 | Value2 |
|---|---|---|---|---|---|---|---|
| 1 | M | 30 | BN43 | 22 | Diabetes | Pos | - |
| 1 | M | 30 | BN43 | 22 | Metformin | 6 | Pkts |
| 1 | M | 30 | BN43 | 22 | Blood Test | 7 | % |
| 2 | M | 45 | SE12 | 23 | Diabetes | Pos | - |
| 3 | M | 34 | BN12 | 26 | Diabetes | Neg | - |
| 3 | M | 34 | BN12 | 26 | Metformin | 10 | Pkts |
| 3 | M | 34 | BN12 | 26 | COPD | Neg | - |

Patient Vector Definitions (Using the same phenotype definitions as well as newly defined ones)
3 different types of phenotype definitions: Binary (T/F), Value, or Bucketed Value Patient Vector Output

| PK | Gender | AGE | BMI>=20 | Value1 | Value2 |
|----|--------|-------|---------|--------|--------|
| 1  | M      | 30-40 | 1       | 1      | 1      |
| 2  | M      | 40-50 | 1       | 1      | 0      |
| 3  | M      | 30-40 | 1       | 0      | 0      |

SYSTEM AND METHOD FOR PHENOTYPE VECTOR MANIPULATION OF MEDICAL DATA

BACKGROUND

Field of the Invention

Embodiments of the present invention generally relate to observational testing, and, in particular, to a system and method for post-selection variable construction for data in an observational test.

Description of Related Art

Observational studies are an important category of study designs. For some kinds of investigative questions (e.g., related to plastic surgery), randomized controlled trials may not always be indicated or ethical to conduct. Instead, observational studies may be the next best method to address these types of questions. Well-designed observational studies may provide results similar to randomized controlled trials, challenging the belief that observational studies are second-rate. Cohort studies and case-control studies are two primary types of observational studies that aid in evaluating associations between diseases and exposures.

Well-designed randomized controlled trials (RCTs) have held the pre-eminent position in the hierarchy of evidence-based medicine (EBM) as level I evidence. However, RCT methodology, which was first developed for drug trials, can be difficult to conduct for some investigations (e.g., surgical cases). Instead, well-designed observational studies, recognized as level II or III evidence, can play an important role in deriving evidence for such investigations. Results from observational studies are often criticized for being vulnerable to influences by unpredictable confounding factors. However, comparable results between observational studies and RCTs are achievable. Observational studies can also complement RCTs in hypothesis generation, establishing questions for future RCTs, and defining clinical conditions.

Observational studies fall under the category of analytic study designs and are further sub-classified as observational or experimental study designs. The goal of analytic studies is to identify and evaluate causes or risk factors of diseases or health-related events. The differentiating characteristic between observational and experimental study designs is that in the latter, the presence or absence of under-going an intervention defines the groups. By contrast, in an observational study, the investigator does not intervene and rather simply "observes" and assesses the strength of the relationship between an exposure and disease variable. Three types of observational studies include cohort studies, case-control studies, and cross-sectional studies. Case-control and cohort studies offer specific advantages by measuring disease occurrence and its association with an exposure by offering a temporal dimension (i.e., prospective or retrospective study design). Cross-sectional studies, also known as prevalence studies, examine the data on disease and exposure at one particular time point. Because the temporal relationship between disease occurrence and exposure cannot be established, cross-sectional studies cannot assess the cause and effect relationship.

The word "cohort" is used in epidemiology to define a set of people followed over a period of time. In particular, "cohort" refers to a group of people with defined characteristics who are followed up to determine incidence of, or mortality from, some specific disease, all causes of death, or some other outcome.

A well-designed cohort study can provide powerful results. In a cohort study, an outcome-free or disease-free study population is first identified by the exposure or event of interest, and then is followed in time until the disease or outcome of interest occurs. Because exposure is identified before the outcome, cohort studies have a temporal framework to assess causality and thus have the potential to provide the strongest scientific evidence. A cohort study is particularly advantageous for examining rare exposures because subjects are selected by their exposure status, and rates of disease may be calculated in exposed and unexposed individuals over time (e.g. incidence, relative risk). Additionally, an investigator can examine multiple outcomes simultaneously. However, the cohort study may be susceptible to selection bias. A cohort study may be large, particularly to study rare exposures, and require a large sample size and a potentially long follow-up duration of the study design, resulting in a costly endeavor.

Cohort studies may be prospective or retrospective. Prospective studies are carried out from the present time into the future. Because prospective studies are designed with specific data collection methods, it has the advantage of being tailored to collect specific exposure data and may be more complete. A disadvantage of a prospective cohort study may include the long follow-up period while waiting for events or diseases to occur. Thus, this study design is inefficient for investigating diseases with long latency periods and is vulnerable to a high loss to follow-up rate.

In contrast, retrospective cohort studies are better indicated for timely and inexpensive study design. Retrospective cohort studies, also known as historical cohort studies, are carried out at the present time and look to the past to examine medical events or outcomes. A cohort of subjects, selected based on exposure status, is chosen at the present time, and outcome data (i.e. disease status, event status), which was measured in the past, are reconstructed for analysis. An advantage of the retrospective study design analysis is the immediate access to the data. The study design is comparatively less costly and shorter than prospective cohort studies. However, disadvantages of retrospective study design include limited control the investigator has over data collection. The existing data may be incomplete, inaccurate, or inconsistently measured between subjects, for example, by not being uniformly recorded for all subjects.

Conventionally, a cohort study defines the selected group of subjects by predetermined criteria (e.g., exposure to a substance, or having a particular medical condition, etc.) at the start of the investigation. A critical characteristic of subject selection is to have both the exposed and unexposed groups be selected from the same source population. Subjects who are not at risk for developing the outcome should be excluded from the study. The source population is determined by practical considerations, such as sampling. Subjects may be effectively sampled from the hospital, be members of a community, or from a doctor's individual practice. A subset of these subjects will be eligible for the study.

When patient data is analyzed, multiple variables describing a person (e.g., age, gender, body mass index (BMI), whether or not the patient has diabetes, etc.) are manipulated. The multiple variables effectively describe criteria that are used as inputs to analysis processes to establish assertions about the statistical nature of the patients in a cohort study. The multiple variables may be represented as a patient vector, which describes the patient's various medical, geographical and demographic variables. The variables generally are produced from the previously described population's raw data, and often is created using covariates.

A problem with this scenario is that the patient cohort definition and the output patient vector are produced in very different ways. Both the patient cohort definition and the output patient vectors require a deep understanding of the underlying data and how to construct clinical criteria in that data, both for data selection and for analytical variable creation. This requires full unfettered access to this data to produce the necessary criteria. This activity would normally be undertaken using scripts and code on a per study, per data set basis.

Attempts have been made and have failed to adequately address the calculation of inferred selection criteria, and inferred analytical variable construction from an observed population. Attempts in the background art generally involve use set theory visualization to compare population across two attributes or data variables. However, when population selection may involve as many as 20-40 attributes, a set theory approach lacks scalability. Known solutions only allow comparison of two variables at a time and do not perform a population synthesis. Manual efforts to expand the analysis beyond two variables has many drawbacks, such as requiring costly expert labor to synthesize queries, being relatively slow, and is not adaptable to allow non-technical business users themselves to derive insights from large healthcare datasets.

The demand for data science in health is increasing dramatically and is highlighted as one of the top growth areas across the entire global technology sector. Data scientists are highly skilled individuals with a rare combination of expertise that spans both advanced statistics and computer science. Paradoxically though, a drawback of the background art is that a significant proportion of data science activity is constantly reported as low-level data manipulation (i.e., "data wrangling"). This data manipulation is driven by the necessity to transform native data formats into a vector-based format required by the mathematics underlying data science theory.

However, such manual selection methods for a retrospective cohort study may suffer from limited sample size or selection bias, or excessive cost. Therefore, what is needed is to combine the advantages of a retrospective cohort study without the disadvantages of difficult-to-use tools to define, find, and manipulate a cohort.

SUMMARY

Within the realm of EMR-based data science, and in order to overcome drawbacks of the background art, embodiments in accordance with the present disclosure define phenotypes in order to define a fundamental atomic building block to enable both data subset creation and vector creation, with phenotype vectors being the primary raw material of EMR-based data science. Embodiments provide a systematic process to determine the most significant factors that can be used to approximate a patient population group.

Embodiments in accordance with the present disclosure provide a cohort definition and selection system for a computer having a memory, a central processing unit and a display, the system including: a cohort definition module to configure the memory according to a phenotype vector. The phenotype vector includes a patient ID to uniquely associate the phenotype vector to a patient, a plurality of demographic dimension fields, each demographic dimension field to describe a respective demographic aspect of the patient, a plurality of calculated dimension fields to describe a calculated information related to the patient, a plurality of, potentially recursively defined phenotype-based dimension fields, each phenotype-based dimension field to indicate relevance of the respective phenotype-based dimension field to the patient.

The preceding is a simplified summary of embodiments of the disclosure to provide an understanding of some aspects of the disclosure. This summary is neither an extensive nor exhaustive overview of the disclosure and its various embodiments. It is intended neither to identify key or critical elements of the disclosure nor to delineate the scope of the disclosure but to present selected concepts of the disclosure in a simplified form as an introduction to the more detailed description presented below. As will be appreciated, other embodiments of the disclosure are possible utilizing, alone or in combination, one or more of the features set forth above or described in detail below.

BRIEF DESCRIPTION OF THE DRAWINGS

The above and still further features and advantages of the present invention will become apparent upon consideration of the following detailed description of embodiments thereof, especially when taken in conjunction with the accompanying drawings wherein like reference numerals in the various figures are utilized to designate like components, and wherein:

FIG. 8A illustrates a simplified set of EMR records for persons and events as known in the art;

FIG. 8B illustrates an example of the output using methods known in the art;

Figure 1A:
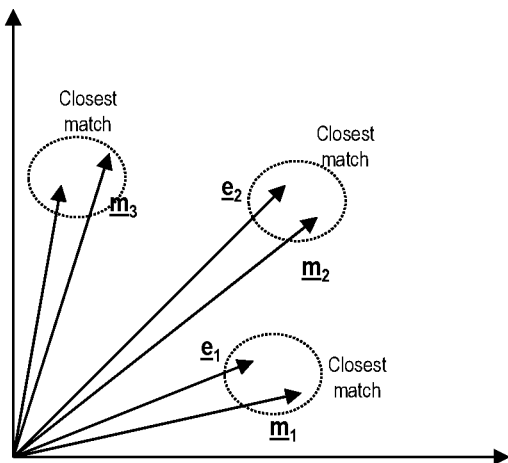
FIGS. 1A, 1B, 1C illustrate vector representations of patient data.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures. Optional portions of the figures may be illustrated using dashed or dotted lines, unless the context of usage indicates otherwise.

DETAILED DESCRIPTION

The disclosure will be illustrated below in conjunction with an exemplary digital information system. Although well suited for use with, e.g., a system using a server(s) and/or database(s), the disclosure is not limited to use with any particular type of system or configuration of system elements. Those skilled in the art will recognize that the disclosed techniques may be used in any system or process in which it is desirable whenever multi-dimensional criteria are used to make an imperfect matching selection from among an available population that shares at least some of these criteria.

The exemplary systems and methods of this disclosure will also be described in relation to software, modules, and associated hardware. However, to avoid unnecessarily obscuring the present disclosure, the following description omits well-known structures, components and devices that may be shown in block diagram form, are well known, or are otherwise summarized.

In the following detailed description, numerous specific details are set forth in order to provide a thorough understanding of embodiments or other examples described herein. In some instances, well-known methods, procedures, components and circuits have not been described in detail, so as to not obscure the following description. Further, the examples disclosed are for exemplary purposes only and other examples may be employed in lieu of, or in combination with, the examples disclosed. It should also be noted the examples presented herein should not be construed as limiting of the scope of embodiments of the present invention, as other equally effective examples are possible and likely.

As used herein, the term "module" refers generally to a logical sequence or association of steps, processes or components. For example, a software module may comprise a set of associated routines or subroutines within a computer program. Alternatively, a module may comprise a substantially self-contained hardware device. A module may also comprise a logical set of processes irrespective of any software or hardware implementation.

A module that performs a function also may be referred to as being configured to perform the function, e.g., a data module that receives data also may be described as being configured to receive data. Configuration to perform a function may include, for example: providing and executing sets of computer code in a processor that performs the function; providing provisionable configuration parameters that control, limit, enable or disable capabilities of the module (e.g., setting a flag, setting permissions, setting threshold levels used at decision points, etc.); providing or removing a physical connection, such as a jumper to select an option, or to enable/disable an option; attaching a physical communication link; enabling a wireless communication link; providing electrical circuitry that is designed to perform the function without use of a processor, such as by use of discrete components and/or non-CPU integrated circuits; setting a value of an adjustable component (e.g., a tunable resistance or capacitance, etc.), energizing a circuit that performs the function (e.g., providing power to a transceiver circuit in order to receive data); providing the module in a physical size that inherently performs the function (e.g., an RF antenna whose gain and operating frequency range is determined or constrained by the physical size of the RF antenna, etc.), and so forth.

As used herein, the term "transmitter" may generally comprise any device, circuit, or apparatus capable of transmitting a signal. As used herein, the term "receiver" may generally comprise any device, circuit, or apparatus capable of receiving a signal. As used herein, the term "transceiver" may generally comprise any device, circuit, or apparatus capable of transmitting and receiving a signal. As used herein, the term "signal" may include one or more of an electrical signal, a radio signal, an optical signal, an acoustic signal, and so forth.

The term "computer-readable medium" as used herein refers to any tangible storage and/or transmission medium that participate in storing and/or providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, RAM, PROM, EPROM, FLASH-EPROM, solid state medium like a memory card, any other memory chip or cartridge, a carrier wave as described here-inafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

At the present time, large-scale routine healthcare databases are amassed and maintained based upon data gathered by healthcare providers and healthcare insurers. For example, a patient who submits to routine health care such as a yearly checkup, regularly-scheduled pap smears or mammograms, or visits for acute but relatively minor problems such as an infection, stitches, or broken bone, will have associated with them a series of healthcare records over time. Healthcare records may also include information related to non-routine care such as emergency room visits, hospital admissions, or other serious healthcare events. The healthcare records may document the progress over time of chronic conditions such as cholesterol levels, high blood pressure, and the like. The healthcare records may also include demographic information such as age, ethnicity, height, weight, and so forth. Because a large portion of the population has access to and uses health care, and the portion may grow in future years due to the Affordable Care Act or its successor, such data is a vast source of information over a large portion or cross-section of the population, representing persons of many different characteristics, risk factors, and so forth. The data for any individual patient may also be available over an extended period of time such as a period of years, so that changes in slowly-progressing medical conditions or slowly-changing patient characteristics may be captured by the data.

In the United Kingdom (UK), such healthcare records may include sources such as the Clinical Practice Research Datalink (CPRD) primary care database (GOLD), the hospital episode statistics (HES) and the Office for National Statistics (ONS) mortality data.

For example, the CPRD, established (initially as GPRD) in the UK in 1987, is a medical records database that general practitioners (GPs) use as the primary means of tracking patient clinical information. The total population in the CPRD exceeds nine million patients with over 35 million person-years of follow-up between 1987 and 2002. About 5% of the UK population is in the CPRD, which is broadly representative of the general UK population in terms of age, sex and geographic distribution. The CPRD, which contains information on diagnoses and medications, was established with the intent of allowing researchers to conduct high quality epidemiologic studies and has been used in more than 200 peer-reviewed publications. All information is recorded by the GP or a member of the office staff as part of the patient's medical record. Approximately 1,500 general practitioners representing 500 practices across the UK participated in the CPRD between 1987 and 2001. GPs are trained in data entry and their data are reviewed by administrators at the CPRD to ensure that they are of sufficient quality for research studies.

Healthcare analysis and research increasing may rely upon the use of such large-scale routine healthcare databases, in particular for retrospective cohort studies. Such databases, because of the coverage over a large portion or cross-section of the population, representing persons of many different characteristics, risk factors, and so forth, may reduce the drawbacks of traditional retrospective cohort studies such as existing data being incomplete, inaccurate, or inconsistently measured between subjects, for example, by not being uniformly recorded for all subjects. Standardized tests for blood work, pap smear, and other routine procedures encourages uniformity and completeness of monitored healthcare parameters.

To work with large-scale routine healthcare databases for any use, the definition of the relevant population under study is the first step and an important step. There may be more than one relevant population, for example, a first population that has developed a particular condition, and a second population that has not developed the particular condition as of the time of selection. The selection criteria form an important part of protocols (i.e., population criteria and analysis plan) used for clinical trial and health outcomes studies.

In observational studies, vectorized data forms the basis of many statistical analysis techniques. A problem of the background art is that patient data is seldom available in vectorized form without significant data manipulation. Patient data is typically transactional and time-based (i.e., "longitudinal"). Patient data primarily includes two classes of data, i.e., "people" and "events". People data refers to the patient or enrollee (e.g., a spouse for spousal insurance coverage), enrollment related data (e.g., dates of coverage, exclusions, deductibles, employer, etc.). Event data refers to things that happen to patients, e.g., diagnoses, therapies, procedures, etc.

Significant, both computational and intellectual data manipulation is required to convert a transactional electronic medical record (EMR) data structure in to a research-ready, vector-based structure. In the background art, this intellectual and computational data manipulation is specific to a native EMR data structure and hence is not readily portable from one data set to another.

The data manipulation (sometimes termed "data wrangling") tends to cover two primary activities. First, it may refer to cutting a subset of data from source databases that are relevant to a study being undertaken. Second, it may refer to creating a research-ready data format for that data, i.e., a vector-based data format that can be used as input to the processes and calculations of data science. Conventionally, data wrangling is low-level labor-intensive, data set specific activity, thus a higher-level, data set portable, less labor-intensive method is needed.

However, embodiments improve upon the background art by recognizing that if the data science processes had been defined with respect to standardized vector formats, then the processes should be portable across different data-sets. This positions a vector format as a central, data-set portable pivot point for data science. In vector form, valuable data science processes (e.g., cohort matching, regression analysis and clustering, described in FIGS. 1A-1C, respectively) may be applied to the vector formats, and help enable the analysis and processes to be more portable from one analytic study to another.

Embodiments in accordance with the present disclosure convert medical data to phenotype vectors. With processes and systems designed around phenotype definitions, data manipulation and vector-production may be largely automated, thus enabling a dramatic increase in data science analytic output, e.g., a four-fold capacity increase may be realized. Furthermore, embodiments help enable portability of data and analytic processes, as opposed to processes tied to a data format that is specific only to a predetermined database. High-level tools for Phenotype vector production have a potential to drive significant gains in output and productivity of data analysis.

Data with multiple attributes may be represented as a vector in a multidimensional space, with each dimension of the vector representing one attribute, and taking on values within an allowable range of values for the attribute. Geometrically, the vector at least in two or three dimensions may be represented as an arrow, with a magnitude and direction in an axis corresponding to the sign and magnitude of a corresponding dimension of the vector.

Two vectors can then be thought of as "close" if the distance between their end-points is small. An error may be calculated as a function of the distance between the vectors. For example, for a vector $\underline{X}=(x_1, x_2, x_3)$ and a vector $\underline{Y}=(y_1, y_2, y_3)$, one measure of the difference between $\underline{X}$ and $\underline{Y}$ is given by Equation (1) below.

$$|\underline{X}-\underline{Y}|=\sqrt{(x_1-y_1)^2+(x_2-y_2)^2+(z_1-z_2)^2} \quad (1)$$

Equation (1) represents the Euclidian geometric distance between the vectors. More generally, different metric functions may be used to define the distance between the vectors taking into account the statistical properties of each dimension for example. Most generally the distance between $\underline{X}$ and $\underline{Y}$ is given by a metric function M as shown below in Equation (2):

$$\text{distance}=|\underline{X}-\underline{Y}|=M(\underline{X},\underline{Y}) \quad (2)$$

In some embodiments, a weighting function may be applied to the difference in each dimension, and for an overall sum. Weighting functions may be useful if the respective vector dimensions have unequal importance for the purpose of patient selection. For example, a distance function (i.e., error function) may take the form shown in Equation (3) for a three-dimensional vector, in which the dimensional weighting functions G( ), H( ) and I( ) may be, e.g., triangle functions, exponential decay functions, step functions, etc., and function F( ) may be, e.g., a summation function, a multiplication, a root, a power, a ratio, or some combination thereof may be used for some dimensions compared to other dimensions, e.g., in order to give unequal weight to different dimensions. However, not all dimensional weighting functions need to be different from other dimensional weighting functions. Equation (3) may be extended to additional dimensions by use of additional weighting functions.

$$|\underline{X}-\underline{Y}|=F(G(x_1-y_1),H(x_2-y_1),I(x_3-y_3)) \qquad (3)$$

Other distance metrics may be used instead of the embodiment shown in Equation (3), as known by persons of skill in the art. For example, a distance metric may include one or more of a Mahalanobis distance metric and a joint weighting function of more than one dimension. A joint function may be useful if, e.g., some dimensions are cross-correlated. For example, separate dimensions for patient weight and patient BMI may be expected to be cross-correlated.

The representations of Equations (1)-(3) are useful because all data science is grounded in some underlying formal mathematical theory, and that mathematical theory is almost entirely vector based.

As applied to analysis of patient data, embodiments may manipulate multiple variables for a single person. Patient characteristics may be represented as a multi-dimensional vector. Patient characteristics may include sociodemographic factors (e.g., age, sex, place of residence, etc.), clinical factors (e.g., comorbidities, medical history, genetic history, blood type, medications used in the week prior to presentation, functional status, immunization history, smoking status, drinking status, etc.), and laboratory data. Dozens of characteristics may be relevant or possibly relevant. Relevancy may be dependent upon the type of study and/or objective of the study, and may be informed by existing medical knowledge. For example, patient weight may be more relevant to a diabetes study than patient eye characteristics, but patient eye characteristics may have more relevance to a study of eye disease. In this case, the selection criteria may give greater weight to characteristics relevant to an objective of selecting the cohort.

FIG. 1A illustrates three patient vectors (i.e., $e_1$, $e_2$, $e_3$) for an exposed cohort, compared to three nearest possible matches in a matched cohort (i.e., $m_1$, $m_2$, $m_3$). Matched patients are found by looking for patient vectors which are nearest in space to each patient in the exposed group, with "nearest" being calculated by a relationship such as one of Equations (1)-(3). There are many additional techniques used for cohort matching (e.g., propensity score matching, principle component analysis, coarsened exact matching, and so forth). Even though these techniques differ in the metric they use to measure the distance between two patient vectors, they all still use vectors as their input.

Figure 1B:
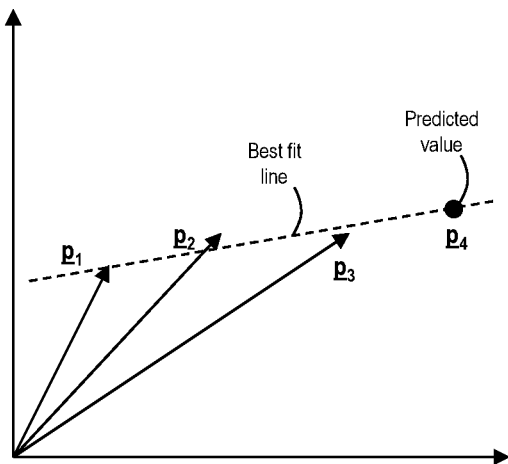

FIG. 1B illustrates usage of a regression analysis technique usable in predictive or interpolative analytics. For example, if $p_1$, $p_2$ and $p_3$ are three patient vectors in a training data set, then $p_4$ may represent a predicted trend given the input data. Given a mathematical model (e.g., a linear trend, a polynomial trend, a seasonally adjusted trend, etc., that may be formulated with knowledge of the underlying causes of the trend), a best fit mathematical equation may be found for the points in space represented by the input vectors and the output to be predicted. These equations then are used to predict the output or outcome for arbitrary patients as represented by their input vectors.

Figure 1C:
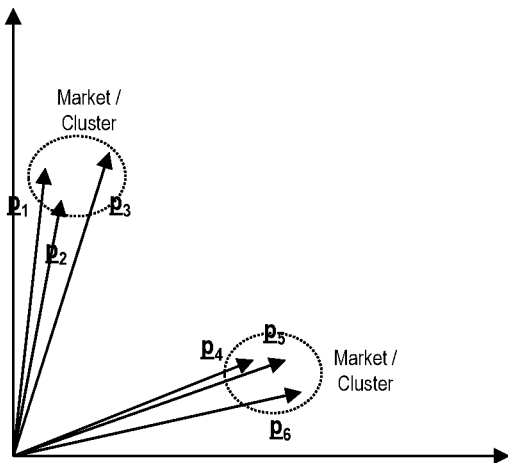

FIG. 1C illustrates an application of clustering processes, which may be used regularly in predictive analytics to predict potential markets for products. For example, $p_1$, $p_2$ and $p_3$ may represent a first market sector or cluster of similar subjects, and $p_4$, $p_5$ and $p_6$ may represent a second market sector or cluster of similar subjects. A distance between points in space represented by vectors is used to identify close neighbors and hence generate clusters of subjects that may be regarded as 'alike'.

In some embodiments, each patient characteristic over a population of patients may be expressed as a statistic that represents the population as a whole. For example, the statistic may be in a form such as a histogram, a series of numeric ranges (e.g., 40-50 years old; 50-60 years old; 150-160 lbs; 160-170 lbs; etc), a series of qualitative ranges (e.g., non-drinker vs. social drinker vs. heavy drinker, etc.), and so forth. Other mathematical representations of the multi-dimensional vector may be possible. Patient characteristics may not be independent of each other, e.g., selection of a female gender characteristic may result in a smaller and lighter population of patients compared to a selection of a male gender characteristic. The data is complex and highly dimensional. Researchers have to make assumptions, based upon science, intuition or other data analysis, that involve structure that is believed to exist in the data but that cannot be observed directly. The data sets are large and growing with a never-ending stream of new data.

Some patients may be classified by use of one or more population codes. The population codes, in turn, represent characteristics of interest to a retrospective cohort study. For example, one population coding system is ICD-10, which is the 10th revision of the International Statistical Classification of Diseases and Related Health Problems (ICD), a medical classification list by the World Health Organization (WHO). ICD-10 codes for diseases, signs and symptoms, abnormal findings, complaints, social circumstances, and external causes of injury or diseases. The code set allows more than 14,400 different codes and permits the tracking of many new diagnoses. The codes can be expanded to over 16,000 codes by using optional sub-classifications. The detail reported by ICD can be further increased, with a simplified multi-axial approach, by using codes meant to be reported in a separate data field.

Another population coding system is the Read code, which is the standard clinical terminology system used in General Practice in the United Kingdom (UK). Read codes support detailed clinical encoding of multiple patient phenomena including: occupation; social circumstances; ethnicity and religion; clinical signs, symptoms and observations; laboratory tests and results; diagnoses; diagnostic, therapeutic or surgical procedures performed; and a variety of administrative items (e.g. whether a screening recall has been sent and by what communication modality, or whether an item of service fee has been claimed). It therefore includes but goes significantly beyond the expressivity of a diagnosis coding system.

Conventionally, synthesis of population selection rules also must be performed manually by such an expert. Synthesis is known as a process of reducing from potentially hundreds of patient population codes to a much smaller set of medical factors, the factors being referred to as inclusion factors or exclusion factors. For example, for a predetermined asthma population (e.g., patients that were initially diagnosed between 12-17 years of age) a medical researcher may decide to look at only patients who were treated with either of two drugs: inhaled corticosteroids (ICS) or fluticasone (i.e., an example of an inclusion criterion). Each of those drugs will have a specific code which usually less recognizable to medical researchers than the drug name itself. In addition to looking at these drugs, a medical researcher may also set another rule to study only patients who were treated in a primary care setting. However, in practice a rule to narrow a study only to patients who were treated in a primary care setting may not be significant because virtually all asthma patients are treated in a primary care setting and thus fails to narrow the population much in practice. Manual synthesis may fail to recognize that such a rule is not significantly meaningful. Thus, manual synthesis may include such a criterion whereas an automated method may recognize that the criterion is not significantly meaningful and thus would not include the criterion in a summary.

In the background art, synthesis of population selection rules is accomplished by constructing detailed queries in a structured language such as SQL. A query may have a large number (e.g., dozens) of components, and be in the form of: ((field_1="value_1") OR (field_1="value_2") AND (field_2="value_3") AND NOT (field_3="value_4") AND . . . OR . . . ). As can be appreciated, this is tedious to construct and difficult to tweak as a desired analytic inquiry changes.

Embodiments in accordance with the present disclosure provide building blocks that may be useful to construct a patient vector to describe each respective patient, and to use the patient vectors to identify patient cohorts for further study. Embodiments may leverage an advantage that arises from having a common vector format used by multiple scientific groups. Embodiments will speed up the research process, allowing a deeper understanding of the methods applied to the common vector format, and allow patient descriptions to be transferred easily between individuals and computer systems.

Embodiments build, extract, and store a common phenotype vector based on multiple patient medical databases, is reusable across multiple projects or studies, and is formatted in a way that isolates users from the underlying data.

Embodiments in accordance with the present disclosure address a problem of vectorizing patient data by creating a framework to define the vector forms, and a system to convert old data to the vector form, and/or enforce the vector form for new data. Phenotypes and phenotype vectors are a useful paradigm to create or reformat vectorized patient data, to define the dimensions of those vectors in a portable manner, and to perform data science on patient data.

A phenotype may be defined as a set of observable characteristics of an individual resulting from the interaction of its genotype with the environment. Embodiments provide a specific implementation that enables rapid, generalized phenotype-vector production from EMR databases. More generally, a phenotype may be defined as an arbitrary Boolean combination of demographic information, code lists, or lists of values representing conditions, drugs, observations, procedures etc. Each code or value list may include some absolute or relative time (i.e., temporal) constraints, and we may additionally specify time relationships between individual lists, e.g., people who have a severe asthma diagnosis after being diagnosed with ADHD.

Figures 2, 3:
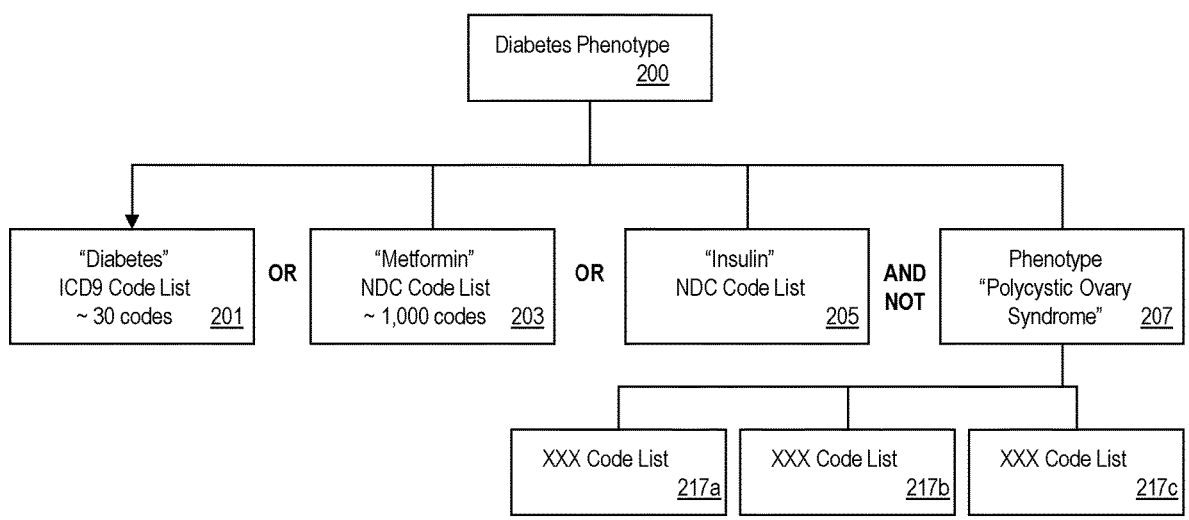
FIG. 2 illustrates an exemplary format for patient data as a phenotype, in accordance with an embodiment of the present disclosure.
FIG. 3 illustrates an exemplary recursive phenotype definition specific to diabetes in accordance with an embodiment of the present disclosure.

FIG. 2 illustrates an exemplary format for patient data as phenotype 200, in accordance with an embodiment of the present disclosure. Phenotype 200 associates a patient ID field 201 with several categories of patient-related data, such as demographic dimensions 203, calculated dimensions 205, and phenotype-based dimensions 207. For example, demographic dimensions 203 may include a binary gender field 231 (e.g., 1="male", 0="female") and a numeric age field 233; calculated dimensions 205 may include an age at index date field 251 and a duration of therapy field 253 (e.g., number of days); phenotype-based dimensions 207 may include a plurality of binary fields, each of which indicates whether the patient indicated by patient ID field 201 is associated with the condition indicated by the respective binary field. For example, an association may include whether (either presently or in the past) the patient has been diagnosed with a predetermined condition, or whether the patient has ever been subject to a predetermined medical procedure, or whether the patient suffers from a predetermined disease or condition. Each binary field may be indicated with 1="true" and 0="false". Exemplary binary fields may include attention deficit hyperactivity disorder (ADHD) field 271, procedure "X" field 272, Asthma field 273, therapy "Y" field 274, and so forth. An exemplary phenotype vector may be $\underline{V}_p(700333xx)=(1, 18, 14, 177, 0, 1, 1, 0, \ldots )$.

A general definition of a phenotype may be expressed in regular expression form as shown below:
Phenotype=Boolean and time related Combination of:
[Lists of conditions (optionally time-bound)|
Lists of drugs (optionally time-bound)|
Lists of observations (optionally time-bound)|
List of procedures (optionally time-bound)|
Phenotypes (optionally time-bound)]

Examples of "time-bound" may include a specification that certain conditions or constraints apply (or do not apply) only over a limited period of time, or only before a predetermined date or event (an event including, e.g., a procedure or an observation), or only after a predetermined date or event, or only in a predetermined sequence (e.g., that a first procedure or observation occurs only before a second procedure or observation, and not after or at the same time as the second procedure or observation), and so forth.

As is evident, phenotypes provide dimensional definition to enable the conversion of EMR data to vectors. Phenotype vectors then can be used as raw material for EMR-based data analytics. Embodiments may include a library of phenotype definitions that provide core templates for both data selection (e.g., though use as inclusion and exclusion criteria) and for vector production (e.g., through use as dimension definitions).

For EMR data, an initial, very simplistic, view of a phenotype might include a single code list—e.g. "does a patient take metformin". This might expand to around 1,000 individual different codes, but it is a single phenotype, that will be represented eventually as a single dimension in a phenotype vector for the patient, indicating their metformin usage.

The last clause of the general definition of a phenotype provides a recursive definition. The recursive definition allows an arbitrarily complex phenotypes to be defined by consuming and combining definitions of other, child phenotypes to substantially any level of depth. For example, a top-level phenotype may include a field or code to indicate that a patient suffers from diabetes, and a pointer to a diabetes child phenotype.

FIG. 3 illustrates an exemplary recursive phenotype definition 300 specific to diabetes. Definition 300 may be described in a Boolean sense as shown below in Equation (3)

[Diabetes code list 201] OR [Metformin NDC codelist 203] OR [Insulin NDC codelist 205] AND NOT [Polycystic Ovary Syndrome 207]   (3)

Polycystic Ovary Syndrome 207 itself may be another phenotype, with subfields 217a, 217b, 217c.

Alternate but similar recursive phenotype definitions may be provided in addition to phenotype definition 300. For example, the diabetes phenotype may provide an expansion of a diabetic condition (e.g., type 1, type 2, gestational, whether is taking insulin, A1C level, etc.), and a pointer to further recursed child phenotype such as a Type 2 phenotype. The Type 2 child phenotype in turn may provide an expansion of the type 2 condition, e.g., the presence of absence of relevant genetic conditions such as genetic defects of β-cell function, genetic defects in insulin processing or insulin action, exocrine pancreatic defects, endocrinopathies, infections, prescribed drugs, and so forth. This recursion maybe repeated indefinitely.

Figure 4:
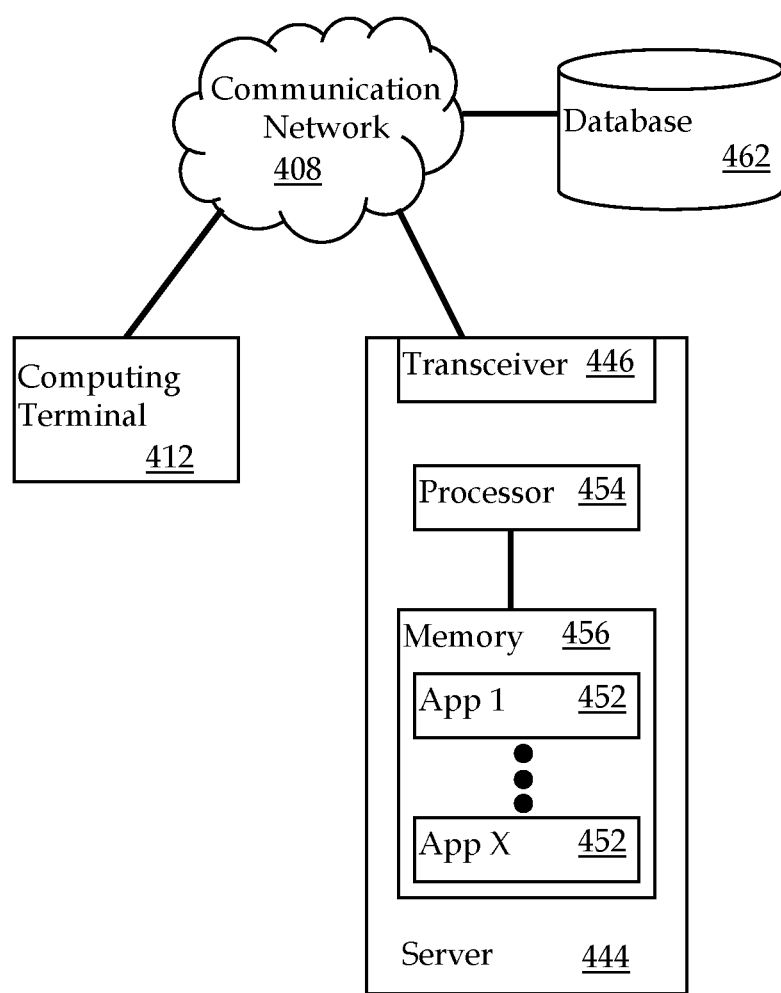
FIG. 4 depicts at a high level of abstraction a system in accordance with an embodiment of the present disclosure.

FIG. 4 depicts at a high level of abstraction a system 400 that may be used in the definition and analysis of cohorts using phenotype vectors, according to an embodiment of the present disclosure. The system 400 may include a communication network 408 that is in communication with computing terminal 412. Exemplary types of external communication devices 412 include, without limitation, desktop Personal Computers (PCs), laptops, netbooks, tablets, thin clients, other smart computing devices, and the like that are accessible via a network. The communication link may operate by methods or protocols such as Ethernet, Wi-Fi, and so forth. The computing power of computing terminal 412 may be used at least in part to manage communications with other portions of system 400 described below.

The communication network 408 may be packet-switched and/or circuit-switched. An exemplary communication network 408 includes, without limitation, a Wide Area Network (WAN), such as the Internet, a Public Switched Telephone Network (PSTN), a Plain Old Telephone Service (POTS) network, a cellular communications network, or combinations thereof. In one configuration, the communication network 408 is a public network supporting the TCP/IP suite of protocols.

System 400 may further include server 444, which is coupled to communication network via transceiver 446. Transceiver 446 may support well-known communication or networking protocols such as Ethernet, Wi-Fi, and so forth. Server 444 may be capable of hosting and/or executing one or more application programs 452 ("apps" or "applications"). For example, server 444 may provide a phenotype execution engine as one of application programs 452. The phenotype execution engine provides a computing platform that allows data scientists to create and to share phenotype definitions, and then to execute those phenotype definitions against large data sets. By executing the phenotype definitions against large data sets, data scientists are able to: (1) rapidly cut data from databases using phenotypes as inclusion and exclusion criteria; and (2) build patient vectors for the selected data using phenotypes as dimension definitions.

Server 444 may be a software-controlled system including a processor 454 coupled to a tangible memory 456. Memory 456 may comprise random access memory (RAM), a read-only memory (ROM), or combinations of these and other types of electronic memory devices. Memory 456 may be used for various purposes such as to store code (e.g., application programs 452) and working memory used by processor 454. Various other server 444 components such as a communication interface modules, power management modules, etc. are known by persons of skill in the art of computer design, but are not depicted in FIG. 4 in order to avoid obscuring the main elements of system 400.

Server 444 may be coupled to a database 462, either directly or through communication network 408 as illustrated in FIG. 4. Database 462 may also be separate from server 444 (as illustrated in FIG. 4), or be incorporated into server 444. Database 462 may be used to store an available universe of patient data (e.g., the GPRD). Database 462 may represent a plurality of physically dispersed databases that are communicatively coupled together.

The elements of system 400 are shown in FIG. 4 for purposes of illustration only and should not be construed as limiting embodiments of the present invention to any particular arrangement of elements. Various other system components such as a gateway, a firewall, etc. are known by persons of skill in the art of computer networking, but are not depicted in FIG. 4 in order to avoid obscuring the main elements of system 400.

Figure 5:
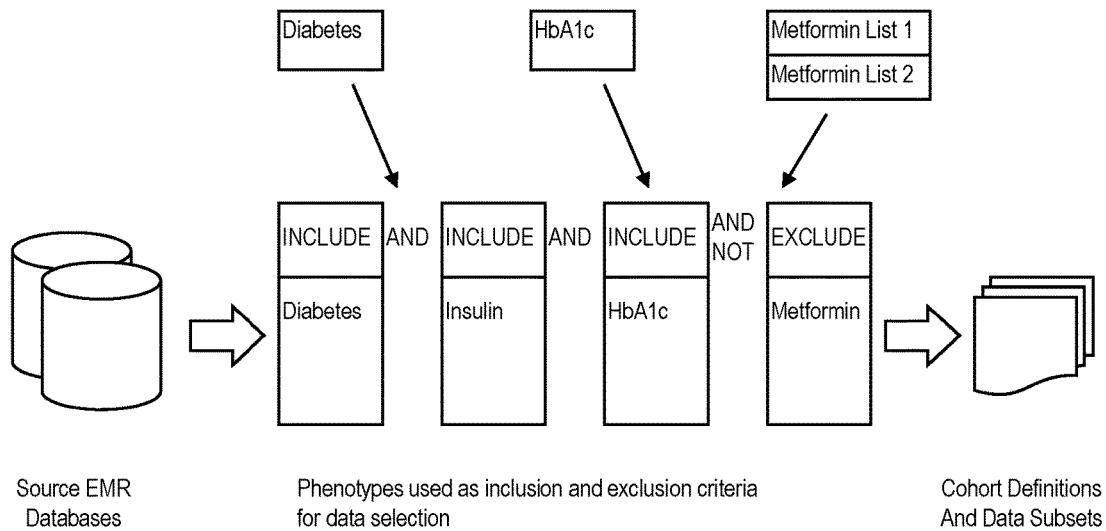
FIG. 5 illustrates a process flow in accordance with an embodiment of the present disclosure.

FIG. 5 illustrates a process flow 500 to use system 400, in accordance with an embodiment of the present disclosure. Process flow 500 would be controlled by a data analyst at computing terminal 412. Data may be read from source EMR databases such as database 462. Database-independent phenotype definitions may be provided by the data analyst, and/or read from a memory such as database 462. The data analyst at computing terminal 412 then may apply or not apply criteria for a study, by way of manipulating phenotype criteria (e.g., inclusion criteria and/or exclusion criteria) for data selection. The data analyst may define and apply these criteria by way of a graphical interface at computing terminal 412 to produce a cohort definition.

FIG. 5 depicts the use of database-independent phenotype definitions to build inclusion and exclusion criteria (i.e., cohort definitions). These cohort definitions can be used across multiple source EMR databases to produce data subsets for subsequent data science-based research. However, at this point the data is not "research ready" because it is not structured as vectors. Instead, the data is still notionally structured in its natural EMR-based format.

Figure 6:
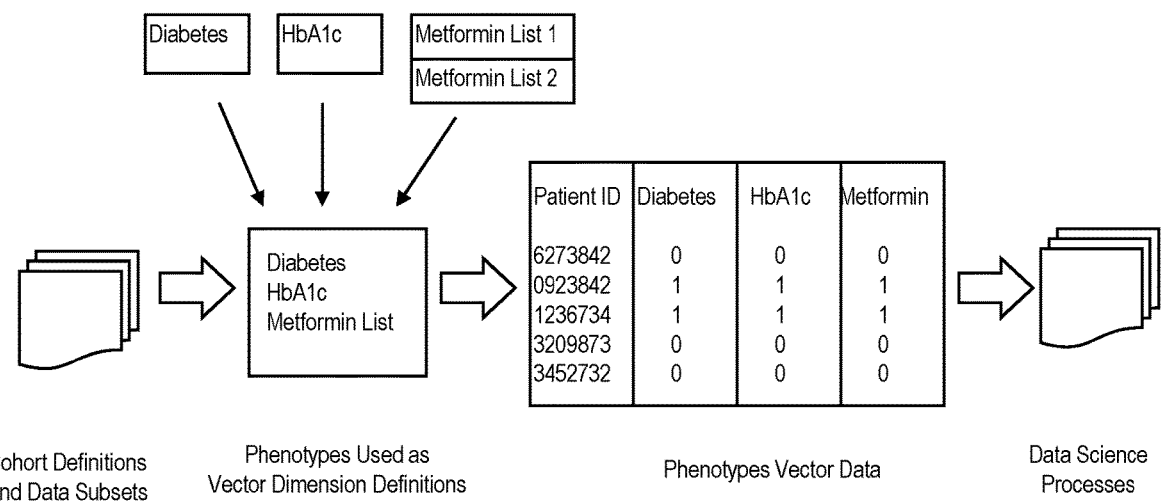
FIG. 6 illustrates a process for a second stage of processing, in accordance with an embodiment of the present disclosure.

FIG. 6 illustrates a process 600 for a second stage of processing. FIG. 6 uses the same library of database-independent phenotype definitions as in process 500, but this time to define vector dimensions. After the cohort definition is determined in process 500, a phenotype engine executing in server 444 (e.g., executing as one of application programs 452) will apply the cohort definition and produce a data subset that meets the cohort definition. The data subset will be returned as phenotype vectors. The data subset then may be stored in a memory (e.g., in a separate portion of database 462) for future study. Once the EMR data subsets are passed through the process of FIG. 6, the subsets are converted to a "research-ready" vector format and can be used as input to data science routines. For example, a set of phenotype vectors meeting the cohort definition and/or processed by the data science routines may be used to identify patients for a cohort study, including identifying patients to recruit if the study is a prospective study.

Figure 7:
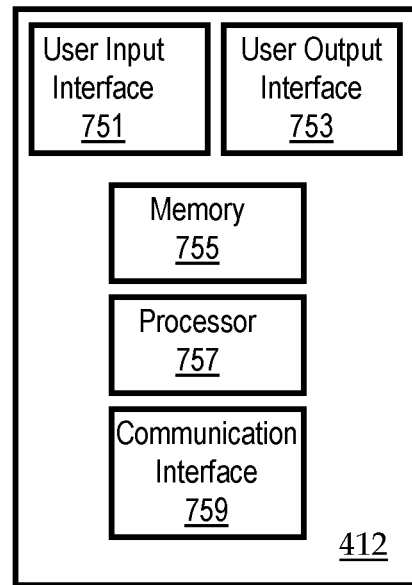
FIG. 7 illustrates components of computing terminal, in accordance with an embodiment of the present disclosure.

FIG. 7 illustrates components of computing terminal 412. As illustrated, in this embodiment, computing terminal 412 is a typical desktop or mobile computing device having basic functions. Computing terminal 412 has a user input interface 751 for receiving input from a user (e.g., a keyboard, touchscreen and/or microphone), and a user output interface 753 is provided for presenting information visually or audibly to the user. Computing terminal 412 also includes memory 755 for storing an operating system that controls the main functionality of computing terminal 412, along with a number of applications that are run on computing terminal 412, and data. A processor 757 executes the operating system and applications. Computing terminal 412 may have a unique hardware identification code that permits identification of computing terminal 412 (e.g., a medium access control (MAC) address). At least a portion of memory 755 may be encrypted. A communications interface 759 permits communications with communication network 108, e.g., by way of an Ethernet or Wi-Fi interface. A user may use computing terminal 412 in order to control the practice of embodiments described herein, and to receive and review results of the embodiments.

FIG. 8A illustrates a simplified set of EMR records for persons and events, in accordance with an embodiment of the present disclosure. The simplified set of EMR records are useful to illustrate a process and paradigm for patient vector generation from existing user generated phenotype definitions. Embodiments support the production of phenotype definitions to be applied to EMR datasets, either singularly or within a time-based Boolean logic expression engine. These phenotype definitions can be codelists, test results and values, demographic details, derived variables and other entities available to embodiments in an EMR dataset, and may recursively include other phenotype definitions.

In the exemplary EMR person structure of FIG. 8A, each patient is assigned a unique patient key (PK), and the patient key is associated with a number of different characteristics for each patient, such as gender, age, geography, BMI, and so forth. In the exemplary EMR event structure, each event is associated with one patient through the PK field, and each event is associated with various characteristics such as event type, and optional value fields relevant to the event type. Any one patient may have any number of associated events, including zero associated events.

In the background art, the structure of FIG. 8A may be interrogated by building simple phenotypes and combining them in Boolean expressions. Time-based criteria may be supplied, instead of or in addition to event-based criteria. Each card may represent one Boolean condition. For example, phenotype_1 may be "Gender=M", phenotype_2 may be "Age=30-50", phenotype_3 may be "BMI≥20" and phenotype_4 may be "EventType=Diabetes". An additional phenotype may be constructed as a Boolean combination of the simple phenotypes, e.g., a Boolean AND of the simple phenotypes, or a more complex relationship including other Boolean operators (e.g., OR, XOR) and parenthetical groupings.

Next, the background art would apply the overall Boolean condition to the patient and event data, and export the result in one of various supported formats, e.g., as a native or single row based view for each patient event. This export type may be relatively large, and contain all data regardless of data science needs. An example of the output using methods of the background art is illustrated in FIG. 8B.

Figures 9A, 9B:
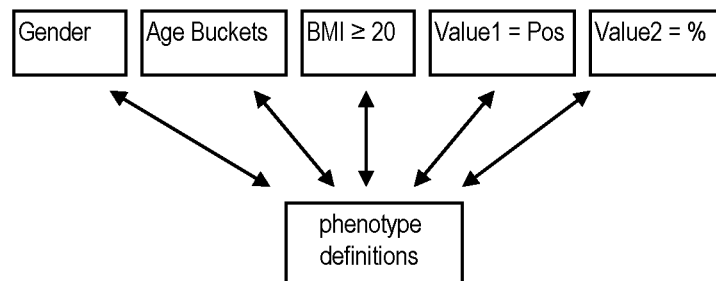
FIG. 9A illustrates a vector-based patient definition, in accordance with an embodiment of the present disclosure.
FIG. 9B illustrates an example of an output, in accordance with the present disclosure.

In contrast, embodiments in accordance with the present disclosure may transform data into a vector-based output, by reusing the phenotype definition paradigm and applying the same definition template structure to a population to create a patient vector. FIG. 9A illustrates a vector-based patient definition, with each phenotype definition representing one of a Boolean condition, a value field, and a bucketed (i.e., range) value. The phenotype definitions can be used to output value-based, value-bucket based or binary (one shot') data in the vector.

FIG. 9B illustrates an example of the output using embodiments in accordance with the present disclosure. Output from the new pivoted view of the data becomes a patient vector, a smaller, more focused output for data science, containing only the values that are required for specific observational research on a population. FIG. 9B illustrates a new data structure that has been derived from the person EMR data, filtered by the criteria of the phenotype definitions, the new data structure being a set of patient vectors in which each element of a respective patient vector is populated by a value within a range defined for the respective element.

Specificity of cohort selection may be limited ultimately by the size of the set of matches that is returned. If the criteria are too narrow, not enough matches will be returned to provide a statistically meaningful sample. Options in this case may include reducing the number of criteria, adjusting error functions in one of Equations (1)-(3) to allow greater error between an ideal characteristic and an actual characteristic, eliminating some selected criteria that may be highly correlated with other selected criteria, substituting one criterion for another if the criteria are correlated but one has a larger available population than the other, and so forth.

Embodiments in accordance with the present disclosure are usable in other fields of study besides cohort definition and selection in medical studies. Embodiments may be useful whenever multi-dimensional criteria are used to make an imperfect matching selection from among an available population that shares at least some of these criteria.

Embodiments of the present invention include a system having one or more processing units coupled to one or more memories. The one or more memories may be configured to store software that, when executed by the one or more processing unit, allows practice of embodiments described herein, including at least as described in the figures and related text.

The disclosed methods may be readily implemented in software, such as by using object or object-oriented software development environments that provide portable source code that can be used on a variety of computer or workstation platforms. Alternatively, the disclosed system may be implemented partially or fully in hardware, such as by using standard logic circuits or VLSI design. Whether software or hardware may be used to implement the systems in accordance with various embodiments of the present invention may be dependent on various considerations, such as the speed or efficiency requirements of the system, the particular function, and the particular software or hardware systems being utilized.

While the foregoing is directed to embodiments of the present invention, other and further embodiments of the present invention may be devised without departing from the basic scope thereof. It is understood that various embodiments described herein may be utilized in combination with any other embodiment described, without departing from the scope contained herein. Further, the foregoing description is not intended to be exhaustive or to limit the invention to the precise form disclosed. Modifications and variations are possible in light of the above teachings or may be acquired from practice of the invention. Certain exemplary embodiments may be identified by use of an open-ended list that includes wording to indicate that the list items are representative of the embodiments and that the list is not intended to represent a closed list exclusive of further embodiments. Such wording may include "e.g.," "etc.," "such as," "for example," "and so forth," "and the like," etc., and other wording as will be apparent from the surrounding context.

No element, act, or instruction used in the description of the present application should be construed as critical or essential to the invention unless explicitly described as such. Also, as used herein, the article "a" is intended to include one or more items. Where only one item is intended, the term "one" or similar language is used. Further, the terms "any of" followed by a listing of a plurality of items and/or a plurality of categories of items, as used herein, are intended to include "any of," "any combination of," "any multiple of," and/or "any combination of multiples of" the items and/or the categories of items, individually or in conjunction with other items and/or other categories of items.

Moreover, the claims should not be read as limited to the described order or elements unless stated to that effect. In addition, use of the term "means" in any claim is intended to invoke 35 U.S.C. § 112(f), and any claim without the word "means" is not so intended.

What is claimed is:

1. A system to select a cohort, the system comprising:
a computer comprising a central processing unit (CPU), the computer configured to:
convert, patient data received from a plurality of databases into a phenotype vector structure, wherein the phenotype vector structure is based on cohort definitions using a format and fields in a plurality of patient, medical, and claims databases;
prepare one or more phenotype vectors, by the CPU, using the phenotype vector structure, wherein the CPU combines the phenotype vector structure with time-based criteria, event-based criteria, and a unique patient key assigned for a respective patient for the observational tests wherein the time-based criteria is independent of the event-based criteria, wherein the event-based criteria includes a medical condition of the respective patient, wherein the unique patient key includes characteristics associated with the respective patient, wherein the phenotype vector structure includes:
a field to uniquely associate the phenotype vectors to the respective patient,
a plurality of demographic fields, each to describe a respective demographics aspect of the respective patient,
a plurality of phenotype-based fields to indicate relevance of a respective demographic field to the respective patient, and
a child phenotype vector to recursively define a phenotype-based field; and
select one or more of the prepared phenotype vectors associated with an error function to form the cohort.

2. The system of claim 1, wherein the one or more phenotype vectors identify patients for a cohort study.

3. The system of claim 1, wherein the phenotype-based fields comprise binary indicators.

4. The system of claim 1, wherein the error function is determined using a Euclidean metric.

5. The system of claim 1, wherein the error function is determined using respective weighting functions for at least one of the demographic dimension fields, the calculated field, and the phenotype-based fields.

6. The system of claim 1, wherein the error function gives greater weight to characteristics relevant to the selection of the cohort.

7. The system of claim 1, wherein at least one of the demographic fields comprises a statistic that represents a patient population as a whole.

8. The system of claim 1, further comprising time relationships between the fields of the phenotype vectors.

9. The system of claim 1, further comprising a time constraint on at least one field of the phenotype vectors.

10. The system of claim 1, wherein a cohort definitions are determined based on a training data set of patient vectors.

11. The system of claim 1, wherein the patients, medical and claims databases are expandable.

12. The system of claim 1, wherein an additional phenotype vector structure is configured to be combined with the time-based criteria, event-based criteria, and the unique patient key when the one or more selected phenotype vectors are not within the predetermined error.

13. A method to select a cohort, the method comprising steps of:
configuring, on a computer, using a Central Processing Unit (CPU), a phenotype vector structure by converting received patient data to the phenotype vector structure from a plurality of databases, wherein the phenotype vector structure is based on cohort definitions using a common format and fields in a plurality of patient, medical, and claims databases, wherein the common format is used by a plurality of scientific groups and does not require knowledge of structures of the plurality of patient, medical, and claims databases;
preparing one or more phenotype vectors by the CPU, using the phenotype vector structure, wherein the CPU combines the phenotype vector structure with time-based criteria, event-based criteria, and the unique patient key for a respective patient for the observational studies, wherein the time-based criteria is independent of the event-based criteria, wherein the event-based criteria includes medical condition of the respective patient, wherein the unique patient key includes characteristics associated with the respective patient, wherein the configured phenotype vector structure includes:
a field to uniquely associate the phenotype vectors to the respective patient,
a plurality of demographic fields, each to describe a respective demographics aspect of the respective patient,
a plurality of phenotype-based fields to indicate relevance of a respective phenotype-based dimension to the respective patient, and
a child phenotype vector to recursively define a phenotype-based field; and
selecting, on the computer, one or more of the prepared phenotype vectors to form the cohort of members from the patient population in the plurality of patient, medical, and claims databases, wherein the two or more phenotype vectors are associated with an error distance to the configured cohort definitions.

14. The method of claim 13, wherein the one or more selected phenotype vectors identify patients for a cohort study.

15. The method of claim 13, wherein the phenotype-based fields comprise binary indicators.

16. The method of claim 13, wherein the error distance is determined using a Euclidean metric.

17. The method of claim 13, wherein the error distance is determined using respective weighting functions for at least one of the demographic dimension fields, the calculated field, and the phenotype-based dimension fields.

18. The method of claim 13, wherein the error distance gives greater weight to characteristics relevant to selecting the cohort.

19. The method of claim 13, wherein at least one of the demographic fields comprises a statistic that represents a patient population as a whole.

20. The method of claim 13, further comprising time relationships between the fields of the phenotype vectors.

21. The method of claim 13, further comprising a time constraint on at least one field of the phenotype vector.

\* \* \* \* \*